(12) United States Patent
Edvardsen et al.

(10) Patent No.: US 8,277,427 B2
(45) Date of Patent: Oct. 2, 2012

(54) FAECAL MANAGEMENT DEVICE

(75) Inventors: Henrik Edvardsen, Koebenhavn (DK); Danuta Ciok, Nivaa (DK); Michael Hansen, Gilleleje (DK); Esben Stroebech, Hoersholm (DK)

(73) Assignee: Coloplast A/S, Humlebaek (DK)

( * ) Notice: Subject to any disclaimer, the term of this patent is extended or adjusted under 35 U.S.C. 154(b) by 196 days.

(21) Appl. No.: 12/672,540

(22) PCT Filed: Aug. 8, 2008

(86) PCT No.: PCT/DK2008/050193
§ 371 (c)(1),
(2), (4) Date: Feb. 8, 2010

(87) PCT Pub. No.: WO2009/021517
PCT Pub. Date: Feb. 19, 2009

(65) Prior Publication Data
US 2010/0168693 A1    Jul. 1, 2010

(30) Foreign Application Priority Data
Aug. 10, 2007  (DK) .............................. 2007 01152

(51) Int. Cl.
*A61F 5/44*   (2006.01)
*A61F 5/458*  (2006.01)

(52) U.S. Cl. ........................................ 604/355; 604/348

(58) Field of Classification Search .......... 604/332–345, 604/348, 355
See application file for complete search history.

(56) References Cited

U.S. PATENT DOCUMENTS

| | | | | | |
|---|---|---|---|---|---|
| 3,018,881 | A | * | 1/1962 | Wall | 206/441 |
| 3,081,771 | A | * | 3/1963 | Lee | 604/344 |
| 3,522,807 | A | * | 8/1970 | Millenbach | 604/355 |
| 3,577,989 | A | * | 5/1971 | Anderson | 604/348 |
| 3,941,133 | A | * | 3/1976 | Chen | 604/336 |
| 4,368,733 | A | * | 1/1983 | Sanidas | 604/327 |
| 4,445,898 | A | * | 5/1984 | Jensen | 604/337 |
| 4,614,183 | A | * | 9/1986 | McCracken et al. | 128/846 |
| 4,681,574 | A | * | 7/1987 | Eastman | 604/344 |
| 4,701,169 | A | * | 10/1987 | Steer | 604/344 |
| 4,834,731 | A | * | 5/1989 | Nowak et al. | 604/339 |
| 4,867,748 | A | * | 9/1989 | Samuelsen | 604/336 |
| 4,894,058 | A | * | 1/1990 | Jensen | 604/332 |
| 5,000,172 | A | * | 3/1991 | Ward | 602/52 |
| 5,384,174 | A | | 1/1995 | Ward et al. | |
| 5,429,592 | A | * | 7/1995 | Jensen | 602/59 |
| 5,593,397 | A | * | 1/1997 | La Gro | 604/355 |

(Continued)

FOREIGN PATENT DOCUMENTS

EP    0753290 A2    1/1997

(Continued)

*Primary Examiner* — Melanie Hand
*Assistant Examiner* — Paula Craig
(74) *Attorney, Agent, or Firm* — Coloplast Corp., Coloplast A/S; Daniel G. Chapik; Nicholas R. Baumann

(57) ABSTRACT

A fecal management device suitable for attachment directly to the perianal skin between the buttocks of the wearer. The device utilizes an optimised adhesive wafer in order to securely attach the device to the skin of the wearer so that the device is maintained in position for the entire period of wear, including circumstances or periods of wear during which the wearer is active, i.e. not bedridden. In addition the fecal management device of the present invention has the ability for easy application of the device.

23 Claims, 5 Drawing Sheets

U.S. PATENT DOCUMENTS

| | | | | |
|---|---|---|---|---|
| 5,695,484 | A * | 12/1997 | Cox | 604/304 |
| 5,704,905 | A * | 1/1998 | Jensen et al. | 602/58 |
| 5,811,116 | A * | 9/1998 | Gilman et al. | 424/443 |
| 5,834,009 | A * | 11/1998 | Sawers et al. | 424/443 |
| 5,998,694 | A * | 12/1999 | Jensen et al. | 602/57 |
| 6,093,160 | A * | 7/2000 | Augustine et al. | 602/2 |
| 6,106,507 | A * | 8/2000 | Botten et al. | 604/338 |
| 6,206,864 | B1 * | 3/2001 | Kavanagh et al. | 604/332 |
| 6,336,920 | B1 * | 1/2002 | Temple | 604/355 |
| 6,350,256 | B1 * | 2/2002 | Palumbo et al. | 604/339 |
| 6,406,464 | B1 * | 6/2002 | Palumbo et al. | 604/355 |
| 6,641,569 | B1 * | 11/2003 | Coles et al. | 604/385.19 |
| 6,685,685 | B2 * | 2/2004 | Sugita et al. | 604/355 |
| 6,685,687 | B2 * | 2/2004 | Mishima et al. | 604/385.19 |
| 6,709,421 | B1 * | 3/2004 | Falconer | 604/335 |
| 7,101,357 | B2 * | 9/2006 | Tanaka et al. | 604/338 |
| 2003/0045843 | A1 * | 3/2003 | Kondo et al. | 604/332 |
| 2003/0204174 | A1 * | 10/2003 | Cisko, Jr. | 604/338 |
| 2004/0087919 | A1 * | 5/2004 | Tanaka et al. | 604/327 |
| 2004/0106908 | A1 * | 6/2004 | Leise et al. | 604/332 |
| 2004/0122384 | A1 * | 6/2004 | Evangelista et al. | 604/346 |
| 2005/0075595 | A1 * | 4/2005 | Hill | 602/41 |
| 2005/0261646 | A1 * | 11/2005 | Conrad et al. | 604/338 |
| 2006/0068146 | A1 * | 3/2006 | Marks et al. | 428/40.1 |
| 2006/0195053 | A1 * | 8/2006 | Oelund et al. | 602/43 |
| 2006/0200101 | A1 * | 9/2006 | Mullejans et al. | 604/339 |
| 2007/0125483 | A1 * | 6/2007 | Barnett et al. | 156/152 |
| 2007/0260206 | A1 * | 11/2007 | Mullejans et al. | 604/332 |
| 2009/0093784 | A1 * | 4/2009 | Hansen et al. | 604/385.05 |
| 2009/0148661 | A1 * | 6/2009 | Stroebech et al. | 428/137 |
| 2011/0137273 | A1 * | 6/2011 | Mullejans et al. | 604/355 |

FOREIGN PATENT DOCUMENTS

| | | |
|---|---|---|
| WO | 0000122 A1 | 1/2000 |
| WO | 03020189 A1 | 3/2003 |
| WO | 2004010911 A1 | 2/2004 |

* cited by examiner

FAECAL MANAGEMENT DEVICE

This application is a national stage of PCT/DK2008/050193 filed Aug. 8, 2008.

FIELD OF THE INVENTION

This invention relates to a faecal management device suitable for attachment directly to the perianal skin between the buttocks of the wearer. The device utilises an optimised adhesive wafer in order to securely attach the device to the skin of the wearer so that the device is maintained in position for the entire period of wear, including circumstances or periods of wear during which the wearer is active, i.e. not bedridden. In addition the faecal management device of the present invention has the ability for easy application of the device.

BACKGROUND OF THE INVENTION

In the intensive care units of hospitals (ICU), the patients often have thin water-like stools, which may be very aggressive to the perianal skin. By perianal is meant the area surrounding the anus opening. For management of stools, diapers, faecal collecting bags or anal invasive products are used. The diapers often result in damaged skin and require frequent change and the invasive products are expensive. Collecting bags attached to the perianal skin are an attractive solution, but the devices on the market today have problems with a high degree of leakage.

Present adhesives for faecal management by means of a collecting bag have poor wear time, leading to possible exposure of faecal output on the perianel skin and to more nursing time. Furthermore, the prior art are mainly describing devices intended for bedridden users and not for mobile or semi-mobile users.

When wearing an adhesive wafer in the perianal area the wafer should be flexible enough in order also to absorb the stress that comes due to body movements.

Hence, it is critical that the faecal management devices are designed so that they are securely attached to the skin of the wearer and do not unintentionally become unattached during any circumstance of use.

WO 00/00122 is describing a faecal management device for babies, children or adults to be attached to the perianal area of the wearer. The device comprises a bag, said bag having an aperture and a skin attachment means surrounding said aperture wherein said skin attachment means meets certain flexibility criteria so as to ensure maintenance of the device in the desired position for the entire period of wear.

The faecal management device may be difficult to apply correctly just as stress may built up in the faecal management device while the user moves and thus cause discomfort and/or leakage.

Thus there is still a need for a faecal management device being easy to apply, comfortable and with good adhesiveness and safety when moving around. The faecal management device of the present invention fulfils these and other objects.

SUMMARY OF THE INVENTION

This invention relates to a faecal management device suitable for attachment directly to the perianal skin between the buttocks of the wearer. Furthermore, the present invention relates to the use of said device.

One object of the present invention is to provide a faecal management device that is easy to apply.

Another object of the invention is to provide a faecal management device that is safe in operation, flexible and adaptable to anatomical configuration of different users and that reduces the risk of leakage. The device should be conformable to the perianal area and optionally mouldable to the skin.

DETAILED DESCRIPTION OF THE INVENTION

Figure 1:
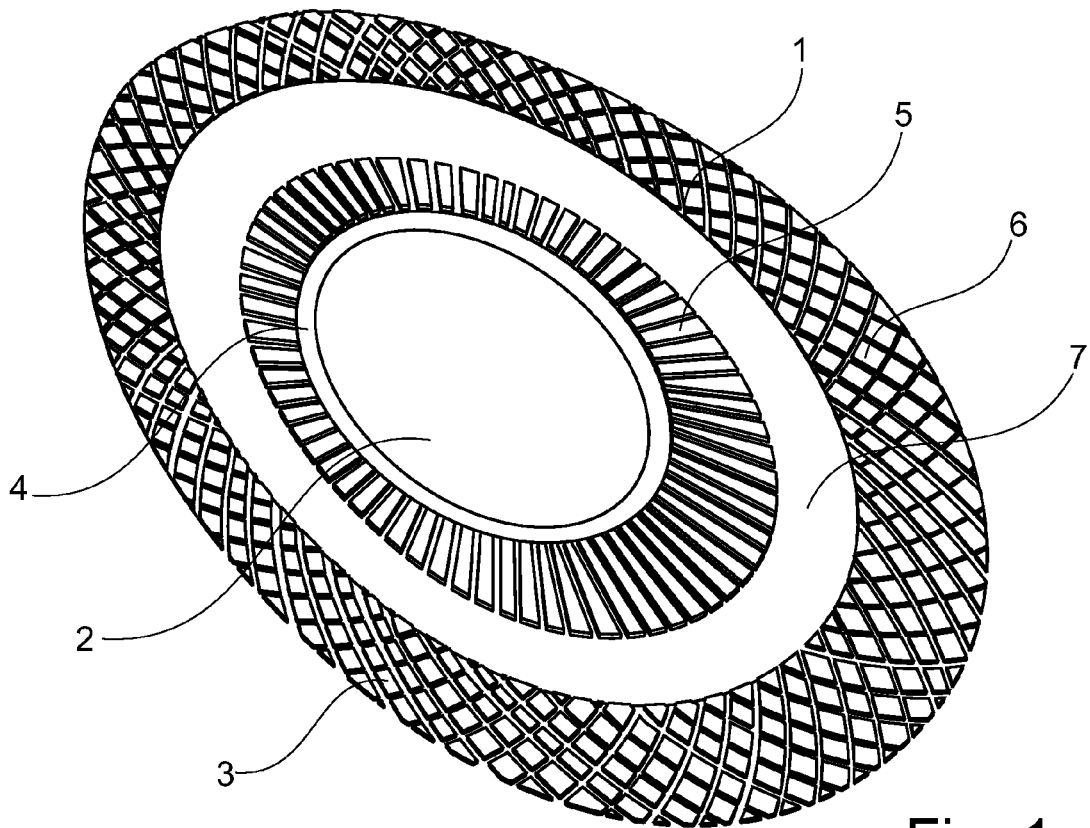
FIG. 1 illustrating the side view of the adhesive wafer showing examples of bevelling and embossment lines, enhancing the flexibility.

The present invention relates to a faecal management device comprising an adhesive wafer wherein the wafer is pre-bent and the skin attaching adhesive side of the wafer is fully covered by a three parts protecting film.

In one embodiment of the invention, the faecal management device according to the invention is used in the perianal area.

A faecal management device may comprise a collecting pouch or bag and an adhesive wafer for attachment to the body. The adhesive wafer may comprise a carrier film functioning as a backing layer, at least one layer of adhesive and a protecting film covering at least partly the skin facing side of the adhesive.

The adhesive wafer of the invention is covered, in part or fully, by a three parts protecting film to be removed before or during application and functioning as a release liner. A protecting film may for instance be siliconised paper. The film to cover the adhesive of the wafer is releasable. It does not need to have the same contour as the wafer.

In order to improve handling during use, that is easier to apply and more intuitive, the choice for design of release liner system and materials have been improved over prior art.

The design suitable according to the present invention can be a three parts protecting film solution with a first part of the protecting film contacting the area of the coccygeal and perianal parts of the adhesive wafer.

In one embodiment of the invention, the three parts protecting film comprises a first part contacting the middle part of the skin attaching adhesive side of the wafer.

The said first part further extends beyond the contact area or the middle part of the wafer and substantially covers the 2 underlying parts of the protecting film. Thus, in one embodiment of the invention the first part of the protecting film substantially covers the second and the third parts of the protecting film.

As used herein the side protecting film means the second and third parts of the protecting film.

In an embodiment of the invention, the second and the third parts of the protecting film are lying at least partly beneath the first part of the protecting film.

In one embodiment of the invention, the second and the third parts of the protecting film are folded to allow for better access and control when removing them.

In another embodiment of the invention, the second part of the protecting film is aligned on one side of the contact area of the first part and the third part is aligned on the other side. This design enables better and safer application properties of the adhesive wafer to the skin.

Once the first part has been removed from the area of the adhesive wafer intended for the coccygeal and perianal parts the area can readily be applied to the skin. Once securely fastened to the skin the second part of the protecting film can be rolled off while at the same time applying the just revealed area of adhesive to the skin, and then followed by the same procedure for the third part of the protecting film.

In another embodiment of the invention, the first part of the protecting film can be of substantially transparent material, allowing to distinguish it from the other two parts and to give viewing access to the adhesive.

In one embodiment of the invention, the second and the third parts of the protecting film are of substantially coloured material, preferably substantially white material.

As used herein the middle part of the adhesive wafer means the part where the first protecting film (release liner) adheres directly to the skin side surface of the adhesive. The middle part of the adhesive has such a width that the good bonding to the cave of the perianal skin is obtained without excessive bonding to the buttocks in the first step of application of the product. The cave or the perianal area is defined as the "sewing line" extending from the coccyx to the opening of the anus and further to the start of the sexual organ (penis root or labia). The dilemma of applying the adhesive wafer to the perianal area is to be able to place the adhesive in the cave of the perianal area and avoiding the sides of the adhesive to adhere first. If the middle part of the adhesive is too large area it is very likely that the adhesive wafer does not reach the cave of the perianal area resulting in immediate leakage or that the device is pushed to a unsymmetrical position leading to higher risk of leakage.

The middle part extends all the way in the pre-bent symmetrical direction that is intended for the cave part of the perianal area. Thus, the length of the middle part may typically be the length along the bend from one edge of the wafer to the edge of the diametrically opposed side of the wafer. The width of the middle part may typically be perpendicular to the length of the middle part. The middle part of the adhesive may typically have a width of between 5 mm to 30 mm in order to optimise the aforementioned dilemma.

Pre-folding of the adhesive wafer helps the user/caretaker to apply the product to the perianal area in an easy and safe way. Current commercial products are to be bent by the user/caretaker before application to the perianal area. The bending by the user/caretaker him or her elf can result in an asymmetric bend and an asymmetric application in the perianal area leading to reduced wear time or even leakage. Also the bending by the user/caretaker will vary in radius of bending. A low radius will possibly lead to leakage because the adhesive will not adhere on the entire surface and a too high radius of bending will possibly lead to leakage as the adhesive will bond to the sides of the buttocks before bonding to the cave of the perianal area. In the latter situation, if one obtains a bond in the cave of the perianal area anyway, one is likely to introduce stress to the adhesive system as the buttocks tend to pull off the adhesive bonded to the cave eventually leading to leakage.

By pre-bending the adhesive wafer one enhances a symmetrical application with an optimal bending radius for reaching the cave of the perianal area. The bending radius will typically vary from 2 to 8 mm.

Pre-folding can vary from a 180° folding to a 90° folding as the degree of folding is not that important compared to the fact that any pre-folding will lead to a symmetrical fold by the user/caretaker and thus higher possibility of a symmetrical application.

When applying the faecal management device to the perianal area it is very difficult to see where the centre of the anus opening is located. By applying a guiding line to the pre-bent adhesive wafer (preferably on the side protecting film) it is easy to place the device correctly.

In an embodiment of the invention, at least one of the second and the third parts of the protecting film has guiding lines for application In one embodiment of the invention, the side protecting films are coloured in a different colour in the area close to the output-receiving hole.

The adhesive wafer of the invention can have a central axis of symmetry lying in the plane of the wafer, and a hole going through the adhesive wafer having its centre placed on the central axis of symmetry. The hole divides the central axis of symmetry in two parts. In one embodiment, the hole divides the central axis of symmetry in a short part and a long part. The length of both the short part and the long part of the central axis of symmetry is defined by the distance between the peripheral edge of the adhesive wafer and the nearest edge of the hole on said central axis of symmetry. The length of the short part is shorter than the length of the long part.

The anatomy of the perianal area in humans is very diverse. One of the major differences exists between men and women, but the difference between individuals of the same sex is also considerable. Women have a short distance (1.7-3 cm) between the anus and the vagina and the distance from the scrotum to the anus in men is between 3-7 cm.

According to one embodiment of the invention, the hole in said adhesive wafer is preferably essentially circular.

According to another embodiment of the invention, the hole in said adhesive wafer is preferably essentially oval.

A contour for the adhesive wafer of the invention is suitably an oval geometry of 90×80 mm with a 35 mm hole placed 25 mm (the centre of the hole placed 42.5 mm) from the peripheral edge of the adhesive wafer and on the longest axis of symmetry.

In accordance with an embodiment of the invention the adhesive wafer is bevelled.

In one embodiment of the invention, the wafer at least around its outer periphery is bevelled so that its thickness adjacent to its outer edge does not exceed about one quarter of the thickness of its non-bevelled region.

Also the inner periphery of the receiving hole can be bevelled according to the invention. In another embodiment of the invention, the wafer is bevelled inwardly around the aperture.

A series of advantages are obtained by this bevelling of the edges of the adhesive device. The material of the adhesive device will tend to flow due to influences of skin temperature and weak pressures. The adhesive will tend to flow to the portion of the smaller thickness of material in the bevel. A bevelling will be sufficient to prevent the adhesive material from flowing outside the adhesive wafer and thereby prevent smudging of garments, perianal skin or bed linen. This applies to the outer edges of the adhesive wafer. Also the bevelling of the wafer will give a better flexibility to the system especially in combination with an embossment with indentations.

The inner edge of the adhesive device will absorb liquid from the output, and this causes the inner edge of a hydrocolloid adhesive to swell to a higher degree than the remaining parts of the adhesive wafer and thereby the wafer tends to loose the adhesion power to the skin. This will lead to an undesired contact between the faecal output and the perianal skin. The degree of uptake of output into the adhesive from the inner edge of the wafer is, however, proportional to the thickness of the edge and when a bevel of the inner rim is present, the sealing effect will last longer. The lifetime of the device thereby increases. Bevelling in combination with embossment will increase the flexibility and thereby the possibility of bonding to uneven contours of the perianal skin as well as bonding in the rim of the deflecting anus opening.

The physical activity and change of positions of the user give rise to a bending, stretching, or stressing of the appliance. If the adhesive device is sufficiently flexible, the user will hardly notice this effect.

If the flexibility of the appliance is insufficient to take up the stretching, bending and stress, the user will notice the effect and will eventually experience a pain or itching under the appliance. If the adhesion to the skin is broken, the appliance will loosen from the skin and eventually cause a leakage.

Also the ability of the adhesive wafer to absorb the energy coming from bending or stretching will to a larger extent happen in a flexible adhesive wafer.

The flexibility of an adhesive wafer for faecal management can be changed by several means like adjusting thickness of the wafer, choice of adhesive, choice of carrier film, design and embossment.

In one embodiment of the invention, the wafer is embossed.

When embossing the carrier film into the adhesive wafer one introduces flexibility to the system giving benefits to the user and to security. Embossment of an adhesive wafer for the faecal device can be in the outer rim, giving flexibility to the outer perianal area, and in the inner rim, giving flexibility to enhance bonding to the deflecting anus opening. The embossment will be especially efficient in combination with an inner and outer bevelling of the wafer.

It is preferred that the indentations do not form angles of 90° and 180° with the border of the patch.

An adhesive wafer comprising a network of indentations, in which the lines form angles with the border of the wafer of 90° and 180°, respectively, provides a flexible structure, but an attack by a force perpendicular to the border could relatively easily produce a bent perpendicular to the border, which may cause the wafer to loosen. This effect is counteracted by the curvilinear indentations present in the border area of a wafer of the invention wherein the indentations do not form angles of 90° and 180° with the border of the wafer.

In one embodiment of the invention, the wafer comprises a first central area of a relatively high thickness; a second area surrounding the first area, and a third edge area surrounding the second area wherein the third area is provided with a pattern of curvilinear indentations. The second area may be without indentations. In this embodiment, the second area may assist in stopping the propagation of wrinkles or folds from the edge or from a centre hole of the wafer.

In another embodiment of the invention, the first area is provided with a pattern of indentations In another embodiment of the invention, the indentations in the first area comprise a set of "radial" indentations providing flexibility perpendicular to the indentations. The term "radial" as used in the present context is intended not only to comprise directions from the centre of a circle towards the periphery but also to comprise not crossing directions from a central part of e.g. an ellipse or another closed figure towards the periphery thereof.

In a further embodiment, the first area comprises a set of indentations encircling the central part. Indentations of this kind are preferably present together with and crossing a set of radial indentations and providing a markedly increased flexibility in the central area of the wafer and counteract a stiffening or enforcing effect provided by a set of radial indentations.

In a further embodiment of the invention, wherein the indentations in the third area are in the form of two or more series of curvilinear indentations crossing each other, a very high degree of flexibility is obtained in the border area between free skin and neighbouring skin covered by the wafer and furthermore does not provide straight lines facilitating the progressing of a wrinkle or fold. This embodiment is believed rather to deflect such progressing wrinkles or folds thereby reducing the risk of causing a leak.

It has been found suitable when the width of the indentations is in the magnitude from about 0.5 to about 3 millimeters, e.g. 1-2 millimeters, suitably 1.2 millimeters, thereby providing a suitable flexibility. It is suitable when the width of the indentations at a level at the bottom of the indentations is of the same order of magnitude as stated for the width above.

The curvilinear indentations, when the wafer of the invention is seen from above, may suitably be defined by a mathematical function of second or higher order or a hyperbolic function. Such functions give rise to curvilinear patterns such as circles or super-circles, ellipses or super-ellipses, hyperboles and parables or parts thereof.

In an embodiment of the invention, the wafer comprises removal ears.

In a further embodiment of the invention, the removal ears are positioned on each of the longitudinal sides of the wafer.

The removal ears are preferably non-adhesive ears used for grapping the adhesive wafer upon removal.

The adhesive to be used according to the invention has to be of a skin friendly kind. A skin friendly adhesive is an adhesive that has the ability to handle the water that transpires from the skin during wear in order for the skin to stay intact. Also a skin friendly adhesive must be able to adhere to the skin for a time period of 1 hour to several days and be able to be removed without damaging the skin.

Such adhesives may be found in the class of pressure sensitive adhesives optionally formulated with hydrocolloids particles or other water absorbers for absorbing the excess moisture generated form the skin (generally used in the medical sector for skin adhesion) or pressure sensitive adhesives formulated with a high permeability allowing the excess moisture generated from the skin to be transported away from the skin. Common for the solutions is a flexible adhesive wafer that can conform to the contours in the perianal area.

Examples of adhesive wafer constructions suitable according to the invention are thermoplastic rubber, resin, hydrocolloid based adhesives coated to a thermoplastic impermeable film or permeable silicone, silicone like, acrylic or polyurethane pressure sensitive adhesives coated on a permeable film or non-woven.

The design of the invention relates to a pre-bent adhesive wafer of a faecal management device and a protecting film design consisting of 3 separate units. Preferably, one can hold the bending of the adhesive wafer and the first protecting film in place with a holding tool. When pre-bending a product before application one introduces stress to the system and the system tries to regain a planer state. As for the first protecting film, having a limited adhesion area in the middle part of the adhesive, the protecting film will tend to loosen.

When holding the bend in the desired state the stress in the adhesive will be reduced over time, as the adhesive is a slow flowing liquid. When removing the tool for application the adhesive wafer will hold the position substantially until the device is applied to the perianal area.

In one embodiment of the invention, the wafer comprises a tool for holding the wafer pre-folded before application.

The tool for holding can be produced by carton or relative stiff polymers being able to hold the stress from the adhesive wafer. Preferably a bending of more than 180° is desirable, as the "negative angle" will hold the wafer in place by physical means. The holding tool should be bent in a radius close to the radius of the bent adhesive wafer, typical in the range of 2-8 mm. The design of the holding tool can have any shape with the feature of holding the wafer in place by physical means.

In one embodiment of the invention, the tool for holding the wafer pre-folded is used for application of the faecal management device.

The holding tool can be used to assist application of the device to the perianal area. When applying the device the user/caretaker will remove the holding tool. The first protecting film is then removed in order to expose the middle part of the adhesive surface. Then the device is placed in the cave of the perianal area. In order to obtain good adhesion the holding tool can be placed with the bent surface towards the perianal cave in between the two sides of the adhesive wafer and pushed towards the body. Then the side protecting films are removed to finish the application of the device.

In an embodiment of the invention, the device comprises a bag connected to the adhesive wafer.

In one embodiment of the invention, the bag at least partly is covered with non-woven material.

Optionally a filter can be attached to the device in order to allow gasses to escape the bag. The filter will also remove the malodour more or less. Filters for ostomy care are preferably used.

An outlet on the device is optional. An outlet allows emptying the bag thus avoiding a change of the device every time faecal output has been received to the bag.

The faecal management device can be constructed as a one-piece system where the bag is attached by welding to the adhesive wafer or as a two-piece system where the adhesive wafer by a mechanical coupling or by an adhesion coupling is attached to the bag in a releasable way.

When wearing a faecal management in the perianal area, stress is introduced with friction between the bag and cloth, skin, linen or bed, when the body is moving. These induced stresses have to be absorbed by the adhesive placed in the perianal area. If the induced stress is too high the adhesive will tend to loosen, which results in leakage. In order to minimize the stress induced one can design a strap holding the bag essentially loose when moving.

In one embodiment of the invention, the bag has attached a strap for securing the bag to the leg.

The strap can be a rubber band type placed around the upper leg fixating the bag in a loose way. Optionally the fixating of the bag in a loose way can be obtained by adhering the bag to the leg or buttocks with any double sided skin friendly pressure sensitive adhesive.

The invention is illustrated more in detail in FIGS. 1-5.

An oval adhesive wafer 1 with an asymmetrically placed faecal receiving hole 2 is shown in FIG. 1. The adhesive wafer is bevelled in the outer rim 3 and in the inner rim 4. Embossment enhancing flexibility during use is placed in the inner area 5 and the outer area 6. A welding zone for attaching the adhesive wafer is placed in the mid area 7.

Figure 2:
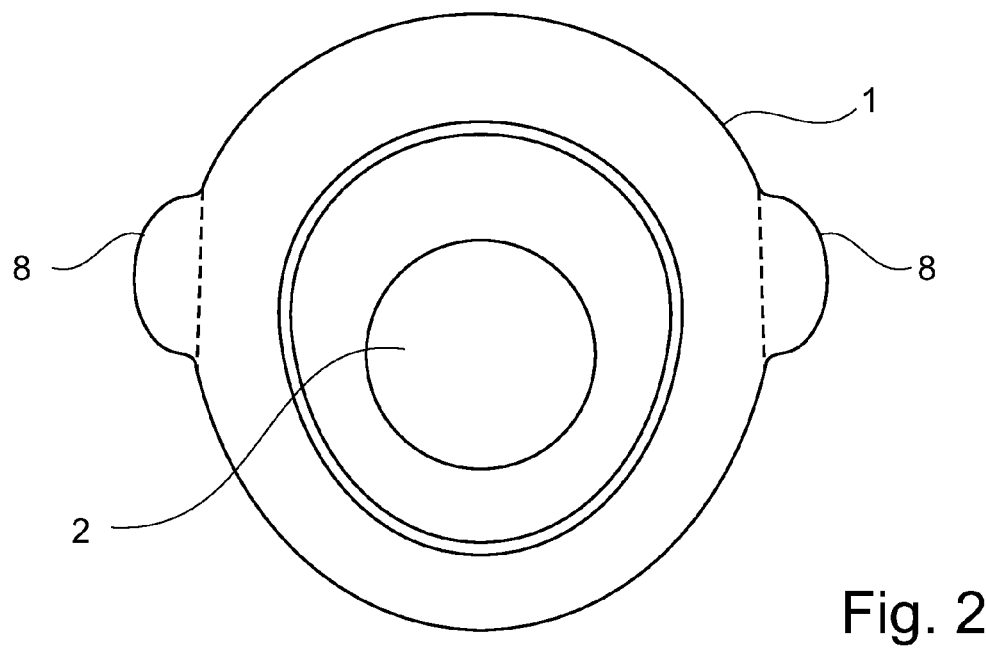
FIG. 2 illustrating an example of the adhesive wafer design including the asymmetric hole and ears for removal.

In FIG. 2 the adhesive wafer 1 is shown with ears for removal 8. The faecal receiving hole 2 has a diameter of 35 mm and the adhesive wafer in its length is 95 mm and in its width 85 mm, not including the ears.

Figure 3:
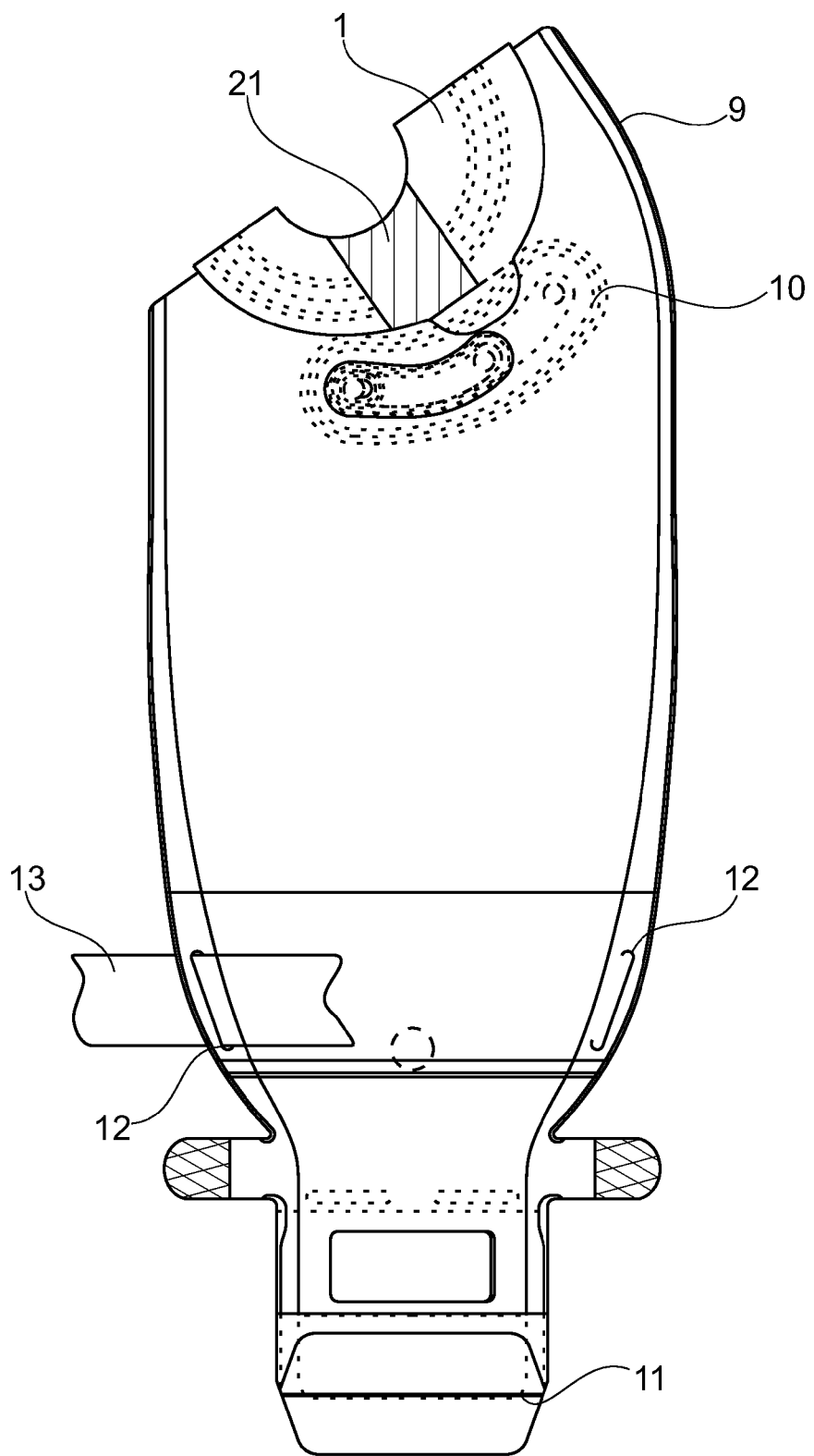
FIG. 3 illustrating an example of the faecal management device according to the invention showing the bending of the adhesive, the filter outlet and the leg strap.

In FIG. 3 the faecal management device 9 is shown visualising the bending of the adhesive wafer 1 in the longitudinal direction. The faecal management device contains a filter 10 for minimising the malodour form the anal gaseous output, an outlet 11 for emptying the device and holes 12 prepared for a strap 13 to hold the device in place on the user ensuring comfort and security. The side protecting films are coloured in a different colour 21 in the area close to the output-receiving hole in order to mark where the centre of the anus is located. The guiding lines will help the user/caretaker to applying the device to the perianal area. The faecal management device 9 is partly covered by a textile giving comfort for the user as close skin contact is present during use (not shown on drawing).

Figure 4:
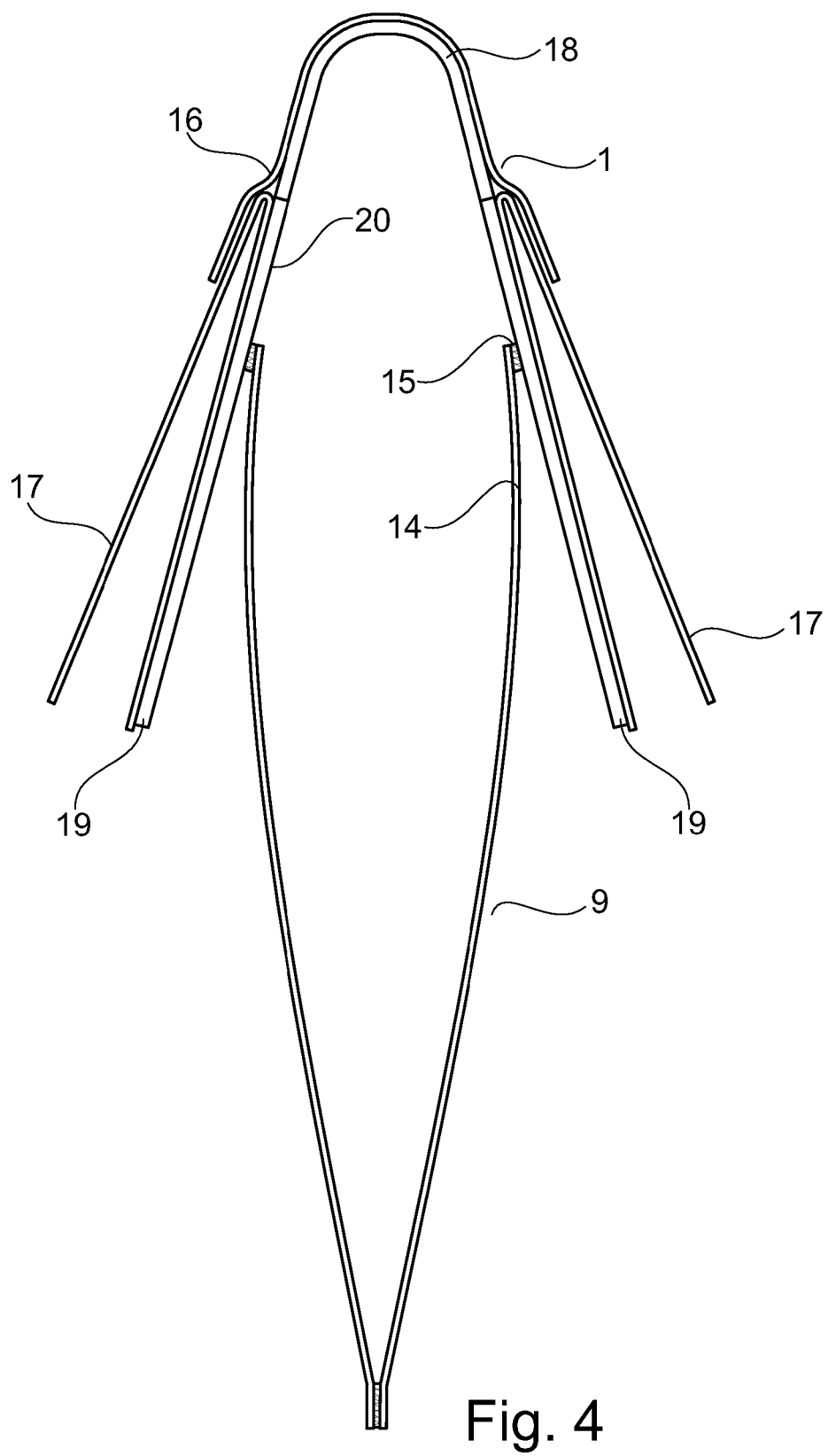
FIG. 4 illustrating the cross section of an example of the faecal management device according to the invention showing the pre-bending of the adhesive wafer and the three parts protecting film construction.

In FIG. 4 the faecal management device 9 is shown as a cut through side view visualising the pre-bend of the adhesive wafer 1 and the attaching means of the bag film 14 to the adhesive film 20 by a welding zone 15.

The protecting film construction is visualised as a pre-bent protecting film 16 covering the middle part of the adhesive 18 and the side protecting films 17 (the second and the third parts of the protecting film) covering the side part of the adhesive 19. The side protecting films 17 are bent into a double layer film. This bending ensures an easy grip of the non-bonded part of the side protecting film 17 and subsequent removal of the side protecting film 17. An easy grip of the non-bonded part of the side protecting film 17 is preferable as the middle part of the adhesive wafer is placed in the perianal area thus restricting the handling of the application.

Figure 5:
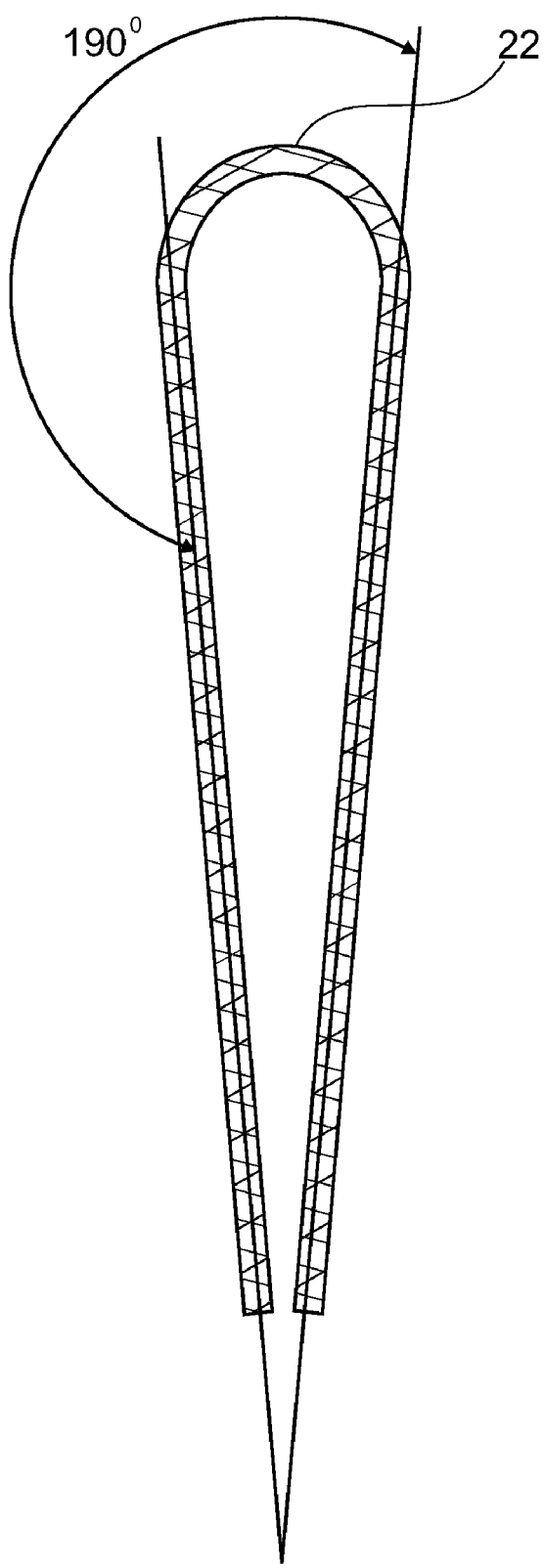
FIG. 5 illustrating an example of a bent holding tool.

In FIG. 5 the bent holding tool 22 is visualised. The stiff polymer film is suitably bent 190° in order to use the resulting mechanical stress forming when the holding tool is opened and the bent adhesive wafer is put into the holding tool.

Figure 6:
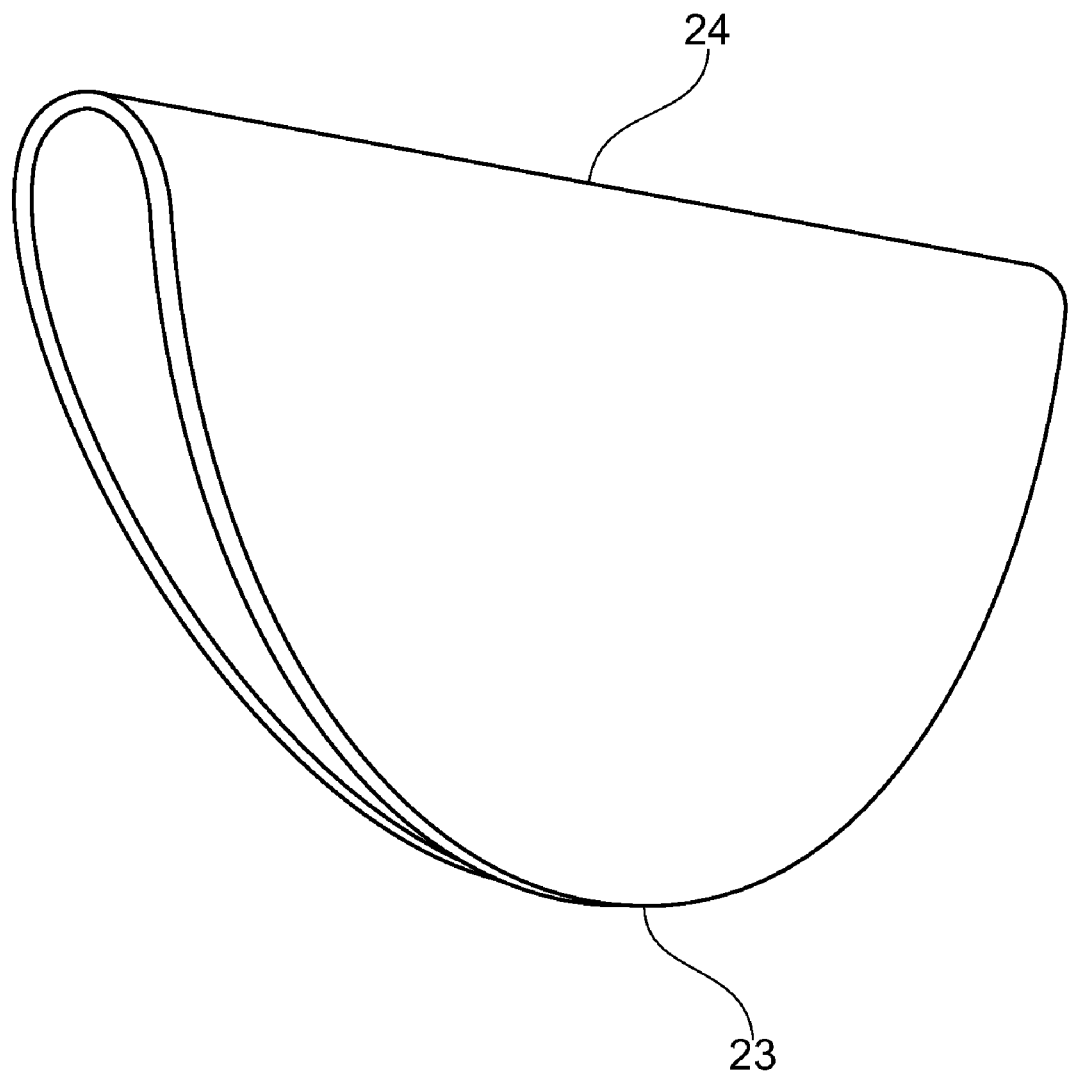
FIG. 6 illustrating an example of a bending tool in a 3D view.

FIG. 6 shows the bending tool in a 3D view. When holding on the curved side 23 with your fingers one can assist application with the bending tool by pressing the bent side 24 towards the cave of the perianal area.

EXPERIMENTAL PART

Example of a Preferred Embodiment

In a preferred embodiment of the invention, a pressure sensitive adhesive wafer with a thickness of 1.2 mm was coated on a linear low density polyethylene film of a thickness of 55 my with an adhesive formulation of 25% styrene-isoprene-styrene copolymer (Kraton D-1163), 35% resin (Arkon P90), 5% plastiziser (Dioctyl adipate), and 35% hydrocolloid (Aquasorb A200). The adhesive wafer had an oval shape of 9×8 cm with an asymmetrically placed hole for receiving the perianal output of a diameter of 30 mm. Two ears for removal were placed in the longitudinal sides of the wafer with a half circle shape of a diameter of 15 mm. The adhesive wafer was pre-bent 180° with a diameter of 10 mm and covered with 3 protecting films. The second and third protecting films were placed in the longitudinal sides of the wafer forming a non-protected middle part of the adhesive wafer with a width of 20 mm. A first protecting film was placed on the entire area of the adhesive wafer, thus only adhering to the middle part of the adhesive wafer. A 300 my amorphous polyethylene terepthalate was bent 190° with a radius of 10 mm and cut into a half circle shape of a diameter of 100 mm. The bent film was placed on top of the bent wafer supporting the wafer and the protecting films. Optionally the stiff, bent film could assist application by using the film for pushing the adhesive wafer into place.

The adhesive wafer forms a faecal management device when a 700 ml bag was attached to the wafer by welding. The film was an odour barrier film Saranex 650 from Dow. The bag contained a filter for reducing mal odour and an outlet for emptying the device. The bag was covered with a non-woven, enhancing the comfort for the user.

The invention claimed is:

1. A faecal management device comprising an adhesive wafer comprising an adhesive surface opposite a non-adhesive surface, wherein the wafer is pre-bent to provide a folded wafer such that the adhesive surface is exposed on an exterior of the folded wafer and configured for placement onto perianal skin between buttocks of a wearer, the adhesive wafer defining a faecal receiving aperture, and the adhesive surface of the wafer is covered by a three-part protecting film including a side film having a marker indicating a location of the faecal receiving aperture.

2. The faecal management device according to claim 1, wherein the wafer is bevelled.

3. The faecal management device according to claim 2, wherein the wafer is bevelled at least around its outer periphery so that a thickness of the wafer adjacent its outer edge does not exceed about one quarter of a thickness of a non-bevelled region of the wafer.

4. The faecal management device according to claim 2, wherein the wafer is bevelled around the faecal receiving aperture.

5. The faecal management device according to claim 1, wherein the wafer is embossed.

6. The faecal management device according to claim 1, wherein the wafer comprises a first central area, a second area surrounding the first area, and a third edge area surrounding the second area, said third area having a pattern of curvilinear indentations.

7. The faecal management device according to claim 6, wherein the first area is provided with a pattern of indentations.

8. The faecal management device according to claim 7, wherein the pattern of indentations in the first area comprises radial indentations.

9. The faecal management device according to claim 6, wherein the first area comprises a set of indentations encircling the central area.

10. The faecal management device according to claim 6, wherein the curvilinear indentations comprise two or more series of curvilinear indentations crossing each other.

11. The faecal management device according to claim 1, wherein the three-part protecting film comprises removal ears that extend past a perimeter of the wafer.

12. The faecal management device according to claim 11, wherein the three-part protecting film comprises a first part configured to cover a central region of the adhesive surface, a second part configured to cover a first outer peripheral region of the adhesive surface, and a third part configured to cover a second outer peripheral region of the adhesive surface, and one of the removal ears is attached to each of the second and third parts of the three-part protecting film and positioned on each longitudinal side of the wafer.

13. The faecal management device according to claim 1, wherein the wafer comprises a tool for holding the folded wafer before application to the perianal skin between the buttocks of the wearer.

14. The faecal management device according to claim 1, wherein the three-part protecting film comprises a first part contacting a middle of the adhesive surface of the wafer.

15. The faecal management device according to claim 14, wherein the first part of the three-part protecting film is substantially transparent.

16. The faecal management device according to claim 14, wherein the wafer has a first lateral side adhesive surface communicating with a second lateral side adhesive surface via the middle adhesive surface, and a second part of the three-part protecting film contacts the first lateral side adhesive surface and a third part of the three-part protecting film contacts the second lateral side adhesive surface.

17. The faecal management device according to claim 16, wherein the second and the third parts of the three-part protecting film are coloured.

18. The faecal management device according to claim 16, wherein at least a portion of the second part and the third part of the three-part protecting film is disposed between the adhesive wafer and the first part of the three-part protecting film.

19. The faecal management device according to claim 16, wherein the first part of the three-part protecting film substantially covers the second part and the third part of the three-part protecting film.

20. The faecal management device according to claim 16, wherein at least one of the second part and the third part of the three-part protecting film includes the marker, the marker provided as guiding lines for application of the adhesive surface to the perianal skin between the buttocks of the wearer.

21. The faecal management device according to claim 1, wherein the device comprises a bag connected to the adhesive wafer.

22. The faecal management device according to claim 21, wherein the bag is covered at least partly with non-woven material.

23. The faecal management device according to claim 21, wherein the bag includes a strap attached to the bag and configured to secure the bag to a leg of the wearer.

* * * * *